US005423794A

United States Patent [19]

Adolf et al.

[11] Patent Number: 5,423,794

[45] Date of Patent: Jun. 13, 1995

[54] INTRAVENOUS CONTAINER WITH SIPHONING PORT

[75] Inventors: Wayne F. Adolf, Mount Prospect; Sheldon M. Wecker, Libertyville, both of Ill.

[73] Assignee: Abbott Laboratories, Abbott Park, Ill.

[21] Appl. No.: 127,834

[22] Filed: Sep. 28, 1993

[51] Int. Cl.[6] .......... A61B 19/00

[52] U.S. Cl. .......... 604/415; 604/403; 604/408; 222/416

[58] Field of Search .......... 604/403, 406–409, 604/415; 128/760, 764, 766, 767, 770; 222/181, 185, 416, 564

[56] References Cited

U.S. PATENT DOCUMENTS 3,064,652 11/1962 Corcoran et al. .......... 604/408
3,707,247 12/1972 Guala .......... 222/416
4,324,349 4/1982 Kaufman .......... 222/185

*Primary Examiner*—David J. Isabella
*Assistant Examiner*—P. Zuttarelli
*Attorney, Agent, or Firm*—A. N. Trausch, III

[57] ABSTRACT

An intravenous container has a siphoning port which permits use with differently sized piercing pins. The container has an access port through which the piercing pin is inserted into the container. A siphon area is provided which is in operative relationship with the access port, is dimensioned to accommodate the piercing pin, and which is in fluid communication with the solution in the container. The piercing pin is inserted into the container through the access port and positioned within the siphon area to create a siphoning effect for maximizing the use of the solution in the container.

7 Claims, 2 Drawing Sheets

INTRAVENOUS CONTAINER WITH SIPHONING PORT

FIELD OF THE INVENTION

The present invention relates to ports for intravenous containers, and more particularly, to siphoning ports for intravenous containers which permit use of differently sized piercing pins.

BACKGROUND OF THE INVENTION

Intravenous containers provide an efficient means for supplying parenteral solutions to a patient. In a typical arrangement, the solution container has an access or discharge port which is connected, in fluid communication, with a tubing set and catheter for infusion of the solution into the patient's body. Generally, the end of the tubing set which is connected to the container discharge port has a hollow piercing pin which serves to pierce a membrane in the discharge port and provide a fluid path for the solution from the container into the tubing set.

In order to efficiently use the solution in the container as the solution level decreases, piercing pins which are sufficiently short must be used to assure that solution continues to flow into the open end of the piercing pin as the solution level within the container drops. This can detract from efficient administration of solutions, since care must be taken to assure use of an appropriately sized piercing pin with the particular container being used.

Accordingly, a solution container with a siphoning port is disclosed in which a siphon chamber or housing is provided to accommodate differently sized piercing pins, and to create a siphon effect through the piercing pin to maximize solution use.

SUMMARY OF THE INVENTION

In accordance with the present invention, a solution container having a siphoning port for use with an associated piercing pin is disclosed which comprises a container body for solution storage and delivery, and an access port joined to the container body which defines a bore for receiving the piercing pin in fluid communication with the solution in the container body. A chamber means within the container body is positioned in operative relationship with the access port. The chamber means is in fluid communication with the solution in the container body and is dimensioned to receive the piercing pin after the piercing pin is inserted through the access port for siphoning solution from within the container body.

In an embodiment of the invention, the solution container has flexible front and back walls and the chamber means is integrally formed with the container. The chamber means comprises a generally inverted U-shaped bonded portion of the front and back walls and defines at least one opening through which solution from within the container body can flow into the chamber means.

In another embodiment of the present invention, the chamber means comprises a hollow housing for receiving the piercing pin, and has at least one opening through which solution from within the container body can flow into the chamber means. In a preferred construction of this embodiment, an annular mounting ring is positioned on the exterior of the container body and extends around the access port. The mounting ring is joined with a peripheral flange portion of the housing and a portion of the container body is disposed between the mounting ring and the peripheral flange portion.

Other features and advantages of the present invention will be apparent from the following detailed description, the accompanying drawings and the appended claims.

DETAILED DESCRIPTION OF PREFERRED EMBODIMENTS

Figure 1:
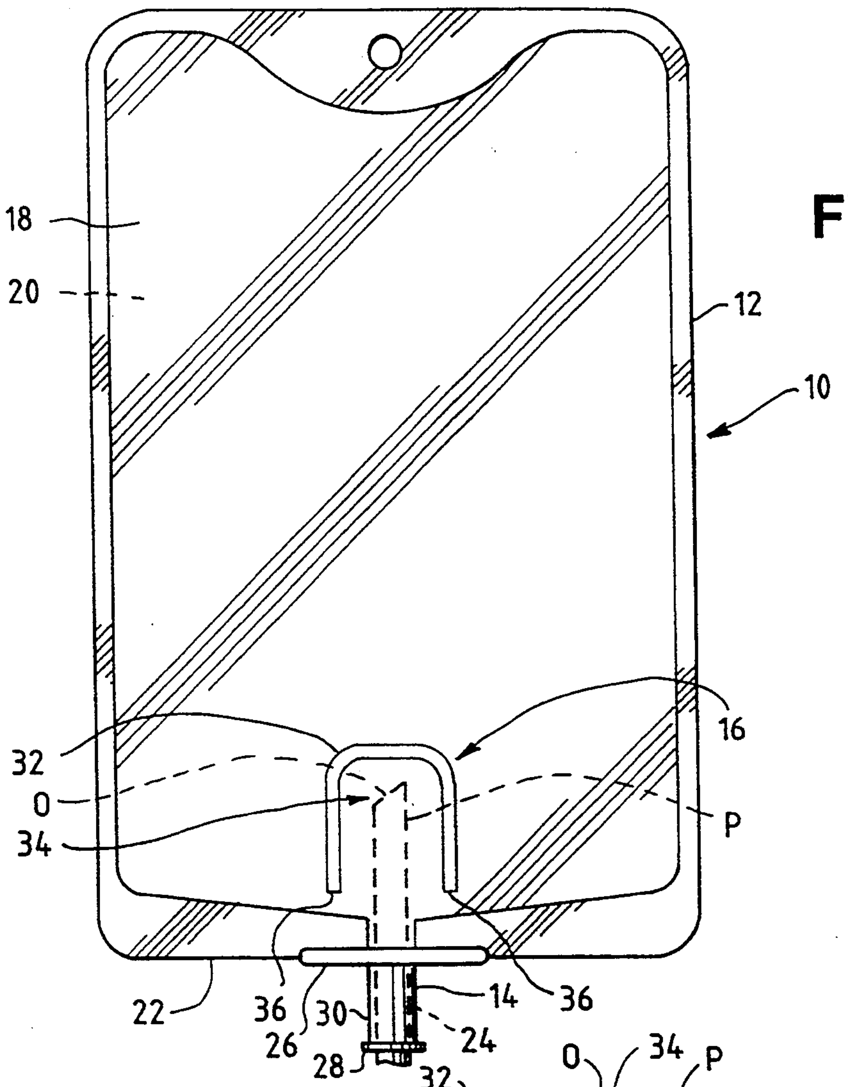
FIG. 1 is a front view of an exemplary solution container showing the container body and siphoning port of the present invention and an associated piercing pin inserted into the solution container.

While the present invention is susceptible of embodiment in various forms, there is shown in the drawings, and will hereinafter be described presently preferred embodiments with the understanding that the present disclosure is to be considered an exemplification of the invention and is not intended to limit the invention to the specific embodiments illustrated.

Figure 2:
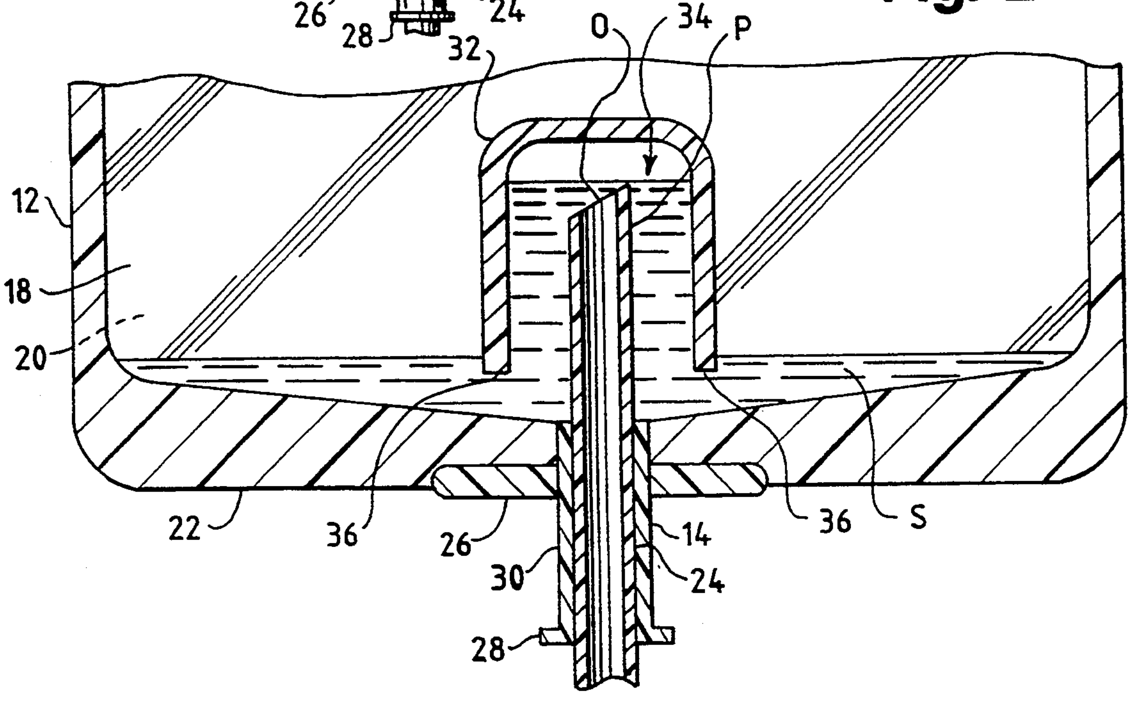
FIG. 2 is a partial cross-sectional view of the lower portion of the solution container showing the siphoning port and illustrating the siphoning effect of the present invention.

With reference now to the drawings, and with particular reference to FIGS. 1 and 2, there is illustrated an embodiment of the present invention showing an exemplary solution container 10 comprising a container body 12, access port 14, chamber means 16, and an associated piercing pin P.

Container body 12 has front and back walls 18, 20 and is preferably fabricated from a flexible plastic material. The outer perimeter of body 12 is sealed through a method such as heat sealing or solvent bonding to form a volume capable of storing solution. The bottom 22 of body 12 is downwardly and inwardly sloped as best seen in FIG. 2 to accommodate pooling of the solution stored therein.

Access port 14 is a hollow cylindrical passageway which defines a bore 24 to accommodate an associated piercing pin P. Port 14 is positioned in the bottom 22 of container body 12 and extends distally 10 therefrom.

First flange 26 extends generally outwardly from access port 14 at the juncture with body 12, and forms a seal between body 12 and access port 14. Flange 26 also serves to provide rigidity to the body-port (12-14) joint. Second flange 28 extends generally radially from about the distal end 30 of port 14 to provide a fingerhold for handling port 14.

Chamber means 16 is formed integral to body 12 and comprises a generally inverted U-shaped barrier 32 which defines siphon area 34 thereunder. Barrier 32 is formed by bonding the front and back walls 18, 20 together preferably through heat sealing, including ultrasonic sealing. The chamber means 16 is positioned within body 12 in operative relationship with access port 14 such that when an associated piercing pin P is inserted through port 14, the piercing pin P extends into the siphon area 34. In forming barrier 32, at least one opening 36 must remain between barrier 32 and bottom 22 such that the solution in siphon area 34 and the solution in container body 12 are in fluid communication. In a preferred construction, barrier 32 is formed so as to define two openings 36, as best seen in FIG. 2.

Figure 3:
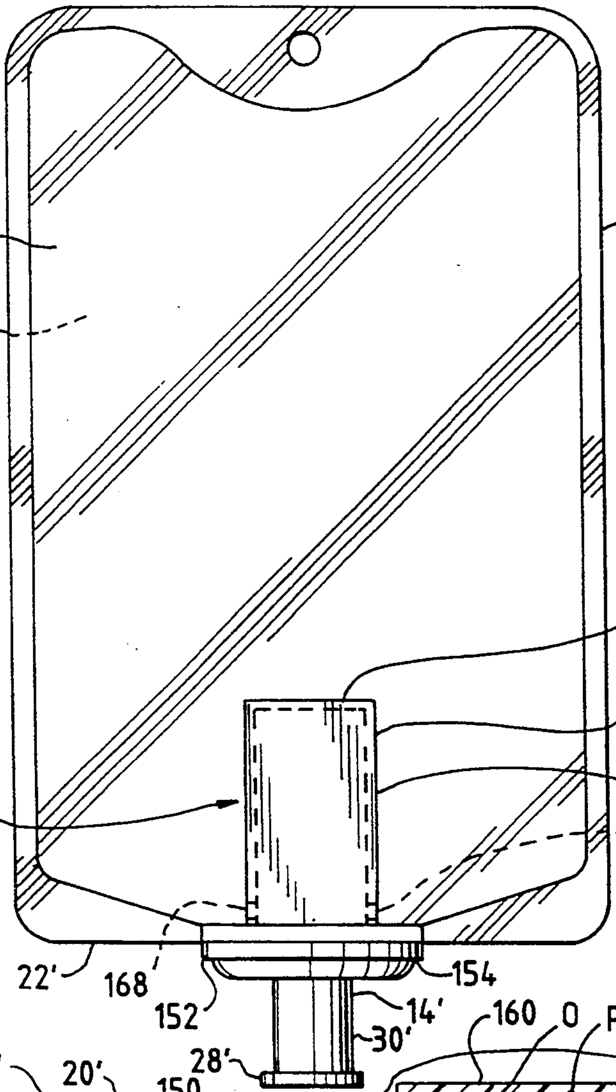
FIG. 3 is a front view of an alternative embodiment of the invention similar to FIG. 1.
Figure 4:
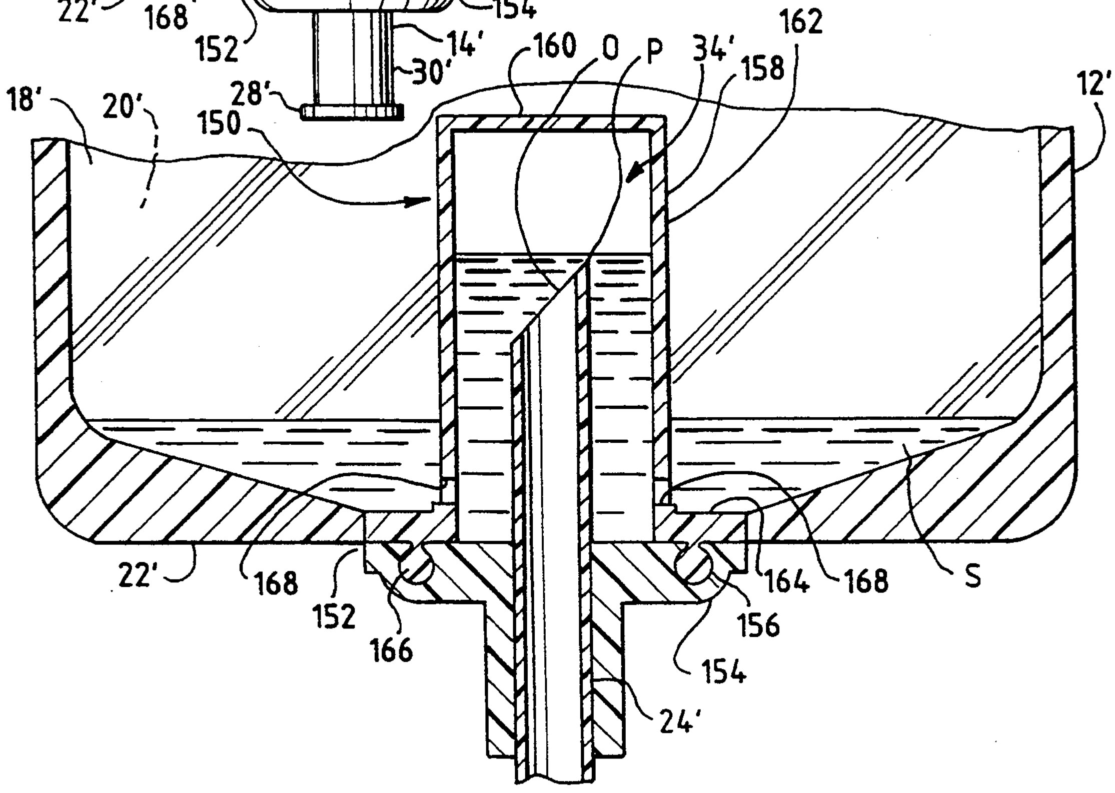
FIG. 4 is a partial cross-sectional view of an alternative embodiment of the present invention similar to FIG. 2.

An alternative embodiment of the present invention is shown in FIGS. 3 and 4 in which, except as shown and described, solution container 10' is similar to solution container 10 and elements designated by primed numbers in FIGS. 3 and 4, correspond to elements designated by the same unprimed numbers in FIGS. 1 and 2. Solution container 10' includes a container body 12', access port 14' and chamber means 150.

Container body 12' has front and back walls 18', 20' and is preferably fabricated from a flexible plastic material. The outer perimeter of body 12' is sealed through a method such as heat sealing or solvent bonding to form a volume capable of storing solution. The bottom 22' of body 12' is downwardly inwardly sloped as best seen in FIG. 4 to accommodate pooling of the stored solution.

Access port 14' has a first flange 152 comprising an annular mounting ring 154, which defines a recessed portion 156. Access port 14' has a second flange 28' extending generally radially from the distal end 30' thereof to provide a finger-hold for handling port 14'.

Chamber means 150 comprises a hollow housing 158 having an upper wall portion 160 and a depending circular side wall portion 162. Side wall portion 162 terminates in a peripheral flange portion 164. Flange portion 164 includes a bead portion 166 extending therefrom for mating with recess 156. At least one opening 168 is formed through side wall portion 162, generally at the juncture of side wall 162 and flange portion 164, for providing fluid communication between the solution within container body 12' and solution internal to housing 158. In a preferred construction, at least two openings 168 are formed through the side wall portion 162.

In assembly of this embodiment, as best shown in FIG. 4, housing 158 is positioned within the container body 12' with the annular mounting ring 154 placed against the bottom 22' of the container body 12'. Access port 14' is positioned outside of body 12' in axial alignment with housing 158. The annular mounting ring 154 and peripheral flange portion 164 are then mated such that bead portion 166 inserts into recess 156 with a portion of the container body 12' disposed or sandwiched therebetween.

Referring now to FIGS. 2 and 4, in use of either embodiment of the present invention, a piercing pin P is inserted into the container body 12, 12', through access port 14, 14'. Pin P is inserted such that the opening 0 is positioned within the siphon area 34, 34'. As the solution S in the container body 12, 12' is drawn through the piercing pin P, solution S freely flows from the container body 12, 12' into the siphon area 34, 34' through openings 36, 168.

When the solution level is above the level of opening O, solution is fed to the piercing pin P via the openings 36, 168. When, however, the solution level in the container body 12, 12' decreases below the level of the opening 0, the solution stream into the siphon area 34, 34' and through the piercing pin P, creates a siphon effect as illustrated in FIGS. 2 and 4. The siphoning effect draws solution into the siphon area 34, 34' from levels below opening 0 of the piercing pin P and maintains the solution within the siphon area 34, 34' at a level sufficient to maintain a continuous flow of solution through the piercing pin P. The result is efficient use of the most practical amount of solution irrespective of the length of the piercing pin P.

From the foregoing, it will be observed that numerous modifications and variations can be effectuated without departing from the true spirit and scope of the novel concept of the present invention. It is to be understood that no limitation with respect to the specific embodiments illustrated is to be intended or should be inferred. The disclosure is intended to cover by the appended claims all such modifications as fall within the scope of the claims.

What is claimed:

1. A solution container for storing a solution and having a port for use with an associated hollow piercing pin having an inlet opening, comprising:

a flexible container body having a sealed interior for storing the solution, and a collapsible exterior;

an access port for delivery of the stored solution, the port having a first end, a second end, and a bore therebetween, the first end associated with the exterior of the container body and the second end associated with the interior of the container body, the port joined to said container body so that the inlet opening in said piercing pin is in fluid communication with the within the interior of said container body when the piercing pin is inserted through the access port; and a siphon chamber in the interior of the container body for continuously siphoning the solution from the interior of the container body through said inlet opening in said piercing pin, said siphon chamber including a lower portion and an upper portion having a siphon area, the lower portion of the siphon chamber positioned within said container body to substantially surround the second end of the access port, the lower portion of the siphon chamber having at least one chamber opening in fluid communication with the solution in said container body and the upper portion of the siphon chamber having a closed end to surround the inlet opening in said piercing pin when said piercing pin is inserted through said access port and the siphon area is located inside the siphon chamber and outside the piercing pin between the lower portion and the closed end of the siphon chamber, the siphon area constructed and arranged to draw solution from the lower portion of the siphon chamber through the siphon area to the inlet opening in the piercing pin.

2. A solution container having a siphon chamber for continuously siphoning in accordance with claim 1 wherein said siphon chamber is integrally formed with said container body.

3. A solution container having a siphon chamber for continuously siphoning in accordance with claim 2 wherein said container body has a flexible front wall and a flexible back wall and said siphon chamber comprises a generally inverted U-shaped portion of said front and back walls defining two chamber openings through which solution from within said container body can flow into said siphon chamber.

4. A solution container having a siphon chamber for continuously siphoning in accordance with claim 3 wherein said flexible front and back walls are bonded by heat sealing.

5. A solution container having a siphon chamber for continuously siphoning in accordance with claim 1 wherein said siphon chamber comprises a hollow housing for receiving said piercing pin, said housing defining two chamber openings therethrough through which solution from within said container body can flow into said siphon chamber.

6. A solution container having a siphon chamber for continuously siphoning in accordance with claim 5 including an annular mounting ring positioned on the exterior of said container body and extending about said access port, said mounting ring being joined with a peripheral flange portion of said housing, with a portion of said container body disposed therebetween for mounting said housing within said container body.

7. A solution container having a siphon chamber for continuously siphoning in accordance with claim 5 wherein said housing comprises an upper wall and a depending circular side wall.

* * * * *